(12) United States Patent
Inoue

(10) Patent No.: US 9,186,246 B2
(45) Date of Patent: Nov. 17, 2015

(54) INTRAOCULAR LENS INSERTION DEVICES AND METHODS

(71) Applicant: HOYA CORPORATION, Tokyo (JP)

(72) Inventor: Masanobu Inoue, Honjo (JP)

(73) Assignee: Hoya Corporation, Tokyo (JP)

( * ) Notice: Subject to any disclaimer, the term of this patent is extended or adjusted under 35 U.S.C. 154(b) by 296 days.

(21) Appl. No.: 13/757,790

(22) Filed: Feb. 2, 2013

(65) Prior Publication Data

US 2013/0245635 A1 Sep. 19, 2013

Related U.S. Application Data

(63) Continuation of application No. 12/997,651, filed as application No. PCT/JP3009/060921 on Jun. 16, 2009, now Pat. No. 8,382,769.

(30) Foreign Application Priority Data

Jun. 17, 2008 (JP) .................................. 2008-158082

(51) Int. Cl.
*A61F 2/16* (2006.01)

(52) U.S. Cl.
CPC ............... *A61F 2/167* (2013.01); *A61F 2/1678* (2013.01)

(58) Field of Classification Search
CPC ... A61F 2/1622; A61F 2/1664; A61F 2/1667; A61F 2/167; A61F 2/1672; A61F 2/1675; A61F 2/1678
USPC .............................. 606/107; 623/6.12; 604/48
See application file for complete search history.

(56) References Cited

U.S. PATENT DOCUMENTS 2,761,446 A 9/1956 Reed
4,205,747 A 6/1980 Gilliam et al.
(Continued)

FOREIGN PATENT DOCUMENTS

DE 3610925 10/1987
DE 4110278 10/1992
(Continued)

OTHER PUBLICATIONS

'Compress' definition from http://dictionary.reference.com/browse/compress accessed on May 18, 2015.*

*Primary Examiner* — Katherine M Shi
(74) *Attorney, Agent, or Firm* — Henricks, Slavin & Holmes LLP

(57) ABSTRACT

There is provided an intraocular lens insertion device capable of easily positioning a circumference of an optical portion of an intraocular lens with respect to a distal end of a plunger. An intraocular lens insertion device 1 comprises: a cartridge 3 having a lens placement section 16 in which an intraocular lens 2 is to be placed; an insertion device main body 4 having a plunger 5 for pushing out the intraocular lens 2 with the cartridge 3 being attached to the insertion device main body 4; and a deforming means 6 for deforming the lens placement section 16. A slit 21 is formed on the lens placement section 16, and the deforming means 6 deforms the lens placement section 16 in a diameter-decreasing direction thereof when attaching the cartridge 3 to the insertion device main body 4. In this way, the intraocular lens 2 is settled at a predetermined position in the lens placement section 16, thus making it possible to position a circumference of an optical portion 2*a* of the intraocular lens 2 with respect to a distal end portion of the plunger 5.

14 Claims, 6 Drawing Sheets

(56) References Cited

U.S. PATENT DOCUMENTS

| | | |
|---|---|---|
| 4,269,307 A | 5/1981 | LaHaye |
| 4,423,809 A | 1/1984 | Mazzocco |
| 4,573,998 A | 3/1986 | Mazzocco |
| 4,608,049 A | 8/1986 | Kelman |
| 4,634,423 A | 1/1987 | Bailey |
| 4,681,102 A | 7/1987 | Bartell |
| 4,697,697 A | 10/1987 | Graham et al. |
| 4,699,140 A | 10/1987 | Holmes |
| 4,702,244 A | 10/1987 | Mazzocco |
| 4,715,373 A | 12/1987 | Mazzocco et al. |
| 4,747,404 A | 5/1988 | Jampel et al. |
| 4,750,498 A | 6/1988 | Graham |
| 4,759,359 A | 7/1988 | Willis et al. |
| 4,763,650 A | 8/1988 | Hauser |
| 4,765,329 A | 8/1988 | Cumming et al. |
| 4,769,034 A | 9/1988 | Poley |
| 4,781,719 A | 11/1988 | Kelman |
| 4,787,904 A | 11/1988 | Severin |
| 4,810,249 A | 3/1989 | Haber et al. |
| 4,819,631 A | 4/1989 | Poley |
| 4,834,094 A | 5/1989 | Patton |
| 4,836,201 A | 6/1989 | Patton |
| 4,862,885 A | 9/1989 | Cumming |
| 4,880,000 A | 11/1989 | Holmes et al. |
| 4,919,130 A | 4/1990 | Stoy et al. |
| 4,934,363 A | 6/1990 | Smith et al. |
| 4,955,889 A | 9/1990 | Van Gent |
| 4,976,716 A | 12/1990 | Cumming |
| 4,988,352 A | 1/1991 | Poley |
| 4,994,028 A | 2/1991 | Leonard et al. |
| 5,066,297 A | 11/1991 | Cumming |
| 5,098,439 A | 3/1992 | Hill et al. |
| 5,123,905 A | 6/1992 | Kelman |
| 5,139,501 A | 8/1992 | Klaas |
| 5,171,241 A | 12/1992 | Buboltz et al. |
| 5,176,686 A | 1/1993 | Poley |
| 5,190,552 A | 3/1993 | Kelman |
| 5,190,553 A | 3/1993 | Kanert et al. |
| 5,222,972 A | 6/1993 | Hill et al. |
| 5,242,450 A | 9/1993 | McDonald |
| 5,259,395 A | 11/1993 | Li |
| 5,275,604 A | 1/1994 | Rheinish et al. |
| 5,281,227 A | 1/1994 | Sussman |
| 5,304,182 A | 4/1994 | Rheinish et al. |
| 5,354,333 A | 10/1994 | Kammann et al. |
| 5,395,378 A | 3/1995 | McDonald |
| 5,425,734 A | 6/1995 | Blake |
| 5,454,818 A | 10/1995 | Hambleton et al. |
| 5,468,246 A | 11/1995 | Blake |
| 5,474,562 A | 12/1995 | Orchowski et al. |
| 5,494,484 A | 2/1996 | Feingold |
| 5,496,328 A | 3/1996 | Nakajima et al. |
| 5,499,987 A | 3/1996 | Feingold |
| 5,562,676 A | 10/1996 | Brady et al. |
| 5,571,113 A | 11/1996 | McDonald |
| 5,578,042 A | 11/1996 | Cumming |
| 5,582,613 A | 12/1996 | Brady |
| 5,582,614 A | 12/1996 | Feingold |
| 5,584,304 A | 12/1996 | Brady |
| 5,616,148 A | 4/1997 | Eagles et al. |
| 5,620,450 A * | 4/1997 | Eagles et al. ............ 606/107 |
| 5,643,275 A | 7/1997 | Blake |
| 5,643,276 A | 7/1997 | Zaleski |
| 5,645,534 A | 7/1997 | Chanoch |
| 5,653,715 A | 8/1997 | Reich et al. |
| 5,653,753 A | 8/1997 | Brady et al. |
| 5,702,402 A | 12/1997 | Brady |
| 5,702,441 A | 12/1997 | Zhou |
| 5,716,364 A | 2/1998 | Makker et al. |
| 5,728,075 A | 3/1998 | Levander |
| 5,728,102 A | 3/1998 | Feingold et al. |
| 5,735,858 A | 4/1998 | Makker et al. |
| 5,766,181 A | 6/1998 | Chambers et al. |
| 5,772,666 A | 6/1998 | Feingold et al. |
| 5,772,667 A | 6/1998 | Blake |
| 5,776,138 A | 7/1998 | Vidal et al. |
| 5,800,442 A | 9/1998 | Wolf et al. |
| 5,803,925 A | 9/1998 | Yang et al. |
| 5,807,400 A | 9/1998 | Chambers et al. |
| 5,810,833 A | 9/1998 | Brady et al. |
| 5,810,834 A | 9/1998 | Heyman |
| 5,860,984 A | 1/1999 | Chambers et al. |
| 5,860,986 A | 1/1999 | Reich et al. |
| 5,868,751 A | 2/1999 | Feingold |
| 5,868,752 A | 2/1999 | Makker et al. |
| 5,873,879 A | 2/1999 | Figueroa et al. |
| 5,876,406 A | 3/1999 | Wolf et al. |
| 5,876,407 A | 3/1999 | Makker et al. |
| 5,876,440 A | 3/1999 | Feingold |
| 5,891,152 A | 4/1999 | Feingold |
| 5,902,307 A | 5/1999 | Feingold et al. |
| 5,919,197 A | 7/1999 | McDonald |
| 5,921,989 A | 7/1999 | Deacon et al. |
| 5,928,245 A | 7/1999 | Wolf et al. |
| 5,941,886 A | 8/1999 | Feingold |
| 5,942,277 A | 8/1999 | Makker et al. |
| 5,944,725 A | 8/1999 | Cicenas |
| 5,947,974 A | 9/1999 | Brady et al. |
| 5,947,975 A | 9/1999 | Kikuchi et al. |
| 5,957,748 A | 9/1999 | Ichiha |
| 5,957,896 A | 9/1999 | Bendek et al. |
| 6,001,107 A | 12/1999 | Feingold |
| 6,010,510 A | 1/2000 | Brown et al. |
| 6,022,358 A | 2/2000 | Wolf et al. |
| 6,048,348 A | 4/2000 | Chambers et al. |
| 6,051,000 A | 4/2000 | Heyman |
| 6,056,757 A | 5/2000 | Feingold et al. |
| 6,056,758 A | 5/2000 | Vidal et al. |
| 6,059,791 A | 5/2000 | Chambers |
| 6,074,397 A | 6/2000 | Chambers et al. |
| 6,083,230 A | 7/2000 | Makker et al. |
| 6,093,193 A | 7/2000 | Makker et al. |
| 6,129,733 A | 10/2000 | Brady et al. |
| 6,142,999 A | 11/2000 | Brady et al. |
| 6,143,000 A | 11/2000 | Feingold |
| 6,162,229 A | 12/2000 | Feingold et al. |
| 6,174,315 B1 | 1/2001 | Chambers et al. |
| 6,214,015 B1 | 4/2001 | Reich et al. |
| 6,241,737 B1 | 6/2001 | Feingold |
| 6,248,111 B1 | 6/2001 | Glick et al. |
| 6,251,114 B1 | 6/2001 | Farmer et al. |
| 6,254,607 B1 | 7/2001 | Makker et al. |
| 6,267,768 B1 | 7/2001 | Deacon |
| 6,283,975 B1 | 9/2001 | Glick et al. |
| 6,283,976 B1 | 9/2001 | Portney |
| 6,312,433 B1 | 11/2001 | Butts |
| 6,334,862 B1 | 1/2002 | Vidal et al. |
| 6,336,932 B1 | 1/2002 | Figueroa et al. |
| 6,355,046 B2 | 3/2002 | Kikuchi et al. |
| 6,371,960 B2 | 4/2002 | Heyman et al. |
| 6,386,357 B1 | 5/2002 | Egawa |
| 6,387,101 B1 | 5/2002 | Butts et al. |
| 6,398,788 B1 | 6/2002 | Makker et al. |
| 6,406,481 B2 | 6/2002 | Feingold et al. |
| 6,428,545 B2 | 8/2002 | Portney |
| 6,447,519 B1 | 9/2002 | Brady et al. |
| 6,447,520 B1 | 9/2002 | Ott et al. |
| 6,468,282 B2 | 10/2002 | Kikuchi et al. |
| 6,471,708 B2 | 10/2002 | Green |
| 6,491,697 B1 | 12/2002 | Clark et al. |
| 6,497,708 B1 | 12/2002 | Cumming |
| 6,500,181 B1 | 12/2002 | Portney |
| 6,506,195 B2 | 1/2003 | Chambers et al. |
| 6,537,283 B2 | 3/2003 | Van Noy |
| 6,540,754 B2 | 4/2003 | Brady |
| 6,554,839 B2 | 4/2003 | Brady |
| 6,558,395 B2 | 5/2003 | Hjertman et al. |
| 6,607,537 B1 | 8/2003 | Binder |
| 6,629,979 B1 | 10/2003 | Feingold |
| 6,666,871 B2 | 12/2003 | Kikuchi et al. |
| 6,679,891 B2 | 1/2004 | Makker et al. |
| 6,685,740 B2 | 2/2004 | Figueroa et al. |
| 6,712,848 B1 | 3/2004 | Wolf et al. |
| 6,723,104 B2 | 4/2004 | Ott |

(56) References Cited

U.S. PATENT DOCUMENTS

| | | |
|---|---|---|
| 6,733,507 B2 | 5/2004 | McNicholas et al. |
| 6,793,674 B2 | 9/2004 | Zapata |
| 6,858,033 B2 | 2/2005 | Kobayashi |
| 6,921,405 B2 | 7/2005 | Feingold et al. |
| 6,923,815 B2 | 8/2005 | Brady et al. |
| 6,976,989 B1 | 12/2005 | Vincent |
| 7,014,641 B2 | 3/2006 | Kobayashi et al. |
| 7,025,782 B2 | 4/2006 | Kobayashi et al. |
| 7,033,366 B2 | 4/2006 | Brady |
| 7,037,312 B2 | 5/2006 | Kikuchi et al. |
| 7,074,227 B2 | 7/2006 | Portney |
| 7,097,649 B2 | 8/2006 | Meyer |
| 7,131,976 B2 | 11/2006 | Kobayashi et al. |
| 7,156,854 B2 | 1/2007 | Brown et al. |
| 7,348,038 B2 | 3/2008 | Makker et al. |
| 7,422,604 B2 | 9/2008 | Vaquero et al. |
| 7,429,263 B2 | 9/2008 | Vaquero et al. |
| 7,458,976 B2 | 12/2008 | Peterson et al. |
| 7,476,230 B2 | 1/2009 | Ohno et al. |
| 7,494,505 B2 | 2/2009 | Kappelhof et al. |
| 7,645,300 B2 | 1/2010 | Tsai |
| 8,273,122 B2 | 9/2012 | Anderson |
| 8,382,769 B2 | 2/2013 | Inoue |
| 8,460,311 B2 | 6/2013 | Ishii |
| 8,470,032 B2 | 6/2013 | Inoue et al. |
| 8,475,528 B2 | 7/2013 | Ichinohe et al. |
| 8,523,877 B2 | 9/2013 | Ichinohe et al. |
| 8,523,941 B2 | 9/2013 | Ichinohe et al. |
| 8,535,375 B2 | 9/2013 | Ichinohe et al. |
| 8,545,512 B2 | 10/2013 | Ichinohe et al. |
| 8,574,239 B2 | 11/2013 | Ichinohe et al. |
| 8,603,103 B2 | 12/2013 | Kudo et al. |
| 8,647,382 B2 | 2/2014 | Kudo et al. |
| 8,702,795 B2 | 4/2014 | Shoji et al. |
| 8,747,465 B2 | 6/2014 | Someya et al. |
| 8,968,328 B2 | 3/2015 | Ichinohe et al. |
| 2001/0007942 A1 | 7/2001 | Kikuchi et al. |
| 2002/0103490 A1 | 8/2002 | Brady |
| 2002/0151904 A1 | 10/2002 | Feingold et al. |
| 2002/0165610 A1 | 11/2002 | Wadlaock |
| 2002/0193805 A1 | 12/2002 | Ott et al. |
| 2003/0036765 A1 | 2/2003 | Van Noy |
| 2003/0040755 A1 | 2/2003 | Meyer |
| 2003/0050647 A1 | 3/2003 | Brady |
| 2003/0088253 A1 | 5/2003 | Seil |
| 2003/0139749 A1 | 7/2003 | Kikuchi et al. |
| 2003/0181921 A1 | 9/2003 | Jeannin |
| 2003/0195522 A1 | 10/2003 | McNicholas |
| 2003/0212406 A1 | 11/2003 | Kobayashi et al. |
| 2003/0212407 A1 | 11/2003 | Kikuchi |
| 2003/0212409 A1 | 11/2003 | Kobayashi et al. |
| 2004/0111094 A1 | 6/2004 | Meyer |
| 2004/0117012 A1 | 6/2004 | Vincent |
| 2004/0127911 A1 | 7/2004 | Figueroa |
| 2004/0186428 A1 | 9/2004 | Ray |
| 2004/0238392 A1 | 12/2004 | Peterson et al. |
| 2004/0243141 A1 | 12/2004 | Brown et al. |
| 2005/0033308 A1 | 2/2005 | Callahan et al. |
| 2005/0049605 A1 | 3/2005 | Vaquero et al. |
| 2005/0049606 A1 | 3/2005 | Vaquero et al. |
| 2005/0055011 A1 | 3/2005 | Enggaard |
| 2005/0125000 A1 | 6/2005 | Tourrette et al. |
| 2005/0143750 A1 | 6/2005 | Vaquero |
| 2005/0182419 A1 | 8/2005 | Tsai |
| 2005/0222578 A1 | 10/2005 | Vaquero |
| 2005/0261703 A1 | 11/2005 | Feingold et al. |
| 2006/0085013 A1 | 4/2006 | Dusek |
| 2006/0142781 A1 | 6/2006 | Pynson et al. |
| 2006/0167466 A1 | 7/2006 | Dusek |
| 2006/0229633 A1 | 10/2006 | Shepherd |
| 2006/0235429 A1 | 10/2006 | Lee et al. |
| 2006/0293694 A1 | 12/2006 | Futamura |
| 2007/0005135 A1 | 1/2007 | Makker et al. |
| 2008/0033449 A1 | 2/2008 | Cole et al. |
| 2008/0058830 A1 | 3/2008 | Cole et al. |
| 2008/0086146 A1 | 4/2008 | Ishii et al. |
| 2008/0097459 A1 | 4/2008 | Kammerlander et al. |
| 2008/0221584 A1 | 9/2008 | Downer |
| 2009/0036898 A1 | 2/2009 | Ichinohe |
| 2009/0043313 A1 | 2/2009 | Ichinohe |
| 2009/0112223 A1 | 4/2009 | Downer et al. |
| 2009/0125034 A1 | 5/2009 | Pynson |
| 2009/0138022 A1 | 5/2009 | Tu et al. |
| 2009/0204122 A1 | 8/2009 | Ichinohe et al. |
| 2009/0216244 A1 | 8/2009 | Pynson |
| 2009/0248031 A1 | 10/2009 | Ichinohe et al. |
| 2010/0161049 A1 | 6/2010 | Inoue |
| 2010/0185206 A1 | 7/2010 | Ichinohe et al. |
| 2010/0217273 A1 | 8/2010 | Someya et al. |
| 2010/0286704 A1 | 11/2010 | Ichinohe et al. |
| 2010/0331808 A1 | 12/2010 | Py et al. |
| 2011/0082463 A1 | 4/2011 | Inoue |
| 2011/0098717 A1 | 4/2011 | Inoue |
| 2011/0264101 A1 | 10/2011 | Inoue et al. |
| 2011/0270264 A1 | 11/2011 | Shoji et al. |
| 2011/0288557 A1 | 11/2011 | Kudo et al. |
| 2012/0022549 A1 | 1/2012 | Someya et al. |
| 2012/0071887 A1 | 3/2012 | Ichinohe et al. |
| 2013/0006259 A1 | 1/2013 | Sanger |
| 2013/0018460 A1 | 1/2013 | Anderson |
| 2013/0226193 A1 | 8/2013 | Kudo et al. |
| 2013/0245635 A1 | 9/2013 | Inoue |
| 2014/0081284 A1 | 3/2014 | Ichinohe et al. |
| 2014/0107660 A1 | 4/2014 | Ichinohe et al. |
| 2014/0114323 A1 | 4/2014 | Kudo et al. |
| 2014/0180299 A1 | 6/2014 | Ichinohe et al. |
| 2014/0180300 A1 | 6/2014 | Ichinohe et al. |
| 2014/0194890 A1 | 7/2014 | Kudo et al. |

FOREIGN PATENT DOCUMENTS

| | | |
|---|---|---|
| EP | 0363213 | 4/1990 |
| EP | 0727966 | 9/2003 |
| EP | 1832247 A1 | 9/2007 |
| EP | 1338254 | 12/2008 |
| FR | 2749752 | 12/1997 |
| JP | 63-197453 A | 8/1988 |
| JP | 4-212350 A | 8/1992 |
| JP | 5-103808 | 4/1993 |
| JP | 5-103809 | 4/1993 |
| JP | 8-024282 A | 1/1996 |
| JP | 8-505540 | 6/1996 |
| JP | 9-506285 A | 6/1997 |
| JP | 11-113939 A | 4/1999 |
| JP | 11-506357 A | 6/1999 |
| JP | 2000-516487 A | 12/2000 |
| JP | 2000-516488 A | 12/2000 |
| JP | 2001-502563 | 2/2001 |
| JP | 2001-104347 A | 4/2001 |
| JP | 2002-516709 A | 6/2002 |
| JP | 2002-355268 A | 12/2002 |
| JP | 2002-541912 A | 12/2002 |
| JP | 2003-144480 A | 5/2003 |
| JP | 3412106 B2 | 6/2003 |
| JP | 2003-210498 A | 7/2003 |
| JP | 2003-325569 A | 11/2003 |
| JP | 2003-325570 A | 11/2003 |
| JP | 2003-325572 A | 11/2003 |
| JP | 2004-024854 A | 1/2004 |
| JP | 2004-188194 A | 7/2004 |
| JP | 2004-351196 A | 12/2004 |
| JP | 2006-181269 A | 7/2006 |
| JP | 2006-297146 A | 11/2006 |
| JP | 2006-333924 A | 12/2006 |
| JP | 2006-333981 A | 12/2006 |
| JP | 2007-503872 A | 3/2007 |
| JP | 2007-152010 A | 6/2007 |
| JP | 2007-181604 A | 7/2007 |
| JP | 2007-526091 A | 9/2007 |
| JP | 2008-521535 A | 6/2008 |
| JP | 2008-212689 A | 9/2008 |
| WO | WO9407436 A1 | 4/1994 |
| WO | WO9513022 A1 | 5/1995 |
| WO | WO9628122 A1 | 9/1996 |

(56) References Cited

FOREIGN PATENT DOCUMENTS

| | | |
|---|---|---|
| WO | WO9715253 A1 | 5/1997 |
| WO | WO9812969 A1 | 4/1998 |
| WO | WO9958086 A1 | 11/1999 |
| WO | WO9959668 A1 | 11/1999 |
| WO | WO0045746 A1 | 8/2000 |
| WO | WO0062712 A1 | 10/2000 |
| WO | WO02071982 A1 | 9/2002 |
| WO | WO02096322 A1 | 12/2002 |
| WO | WO2005023154 A1 | 3/2005 |
| WO | WO2005070341 A1 | 8/2005 |
| WO | WO2005084588 A1 | 9/2005 |
| WO | WO2006070628 A1 | 7/2006 |
| WO | WO2006080191 A1 | 8/2006 |
| WO | WO2006090531 A1 | 8/2006 |
| WO | WO2007037223 A1 | 4/2007 |
| WO | WO2007097221 A1 | 4/2007 |
| WO | WO2007080869 A1 | 7/2007 |
| WO | WO2008149794 A1 | 12/2008 |
| WO | WO2008149795 A1 | 12/2008 |
| WO | WO2009058929 A1 | 7/2009 |
| WO | WO2009148091 A1 | 12/2009 |
| WO | WO2011126144 A1 | 10/2011 |
| WO | WO2011155636 A1 | 12/2011 |

* cited by examiner

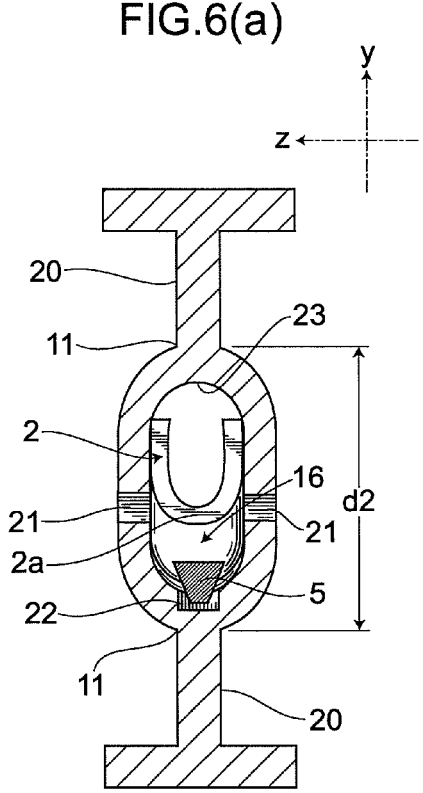
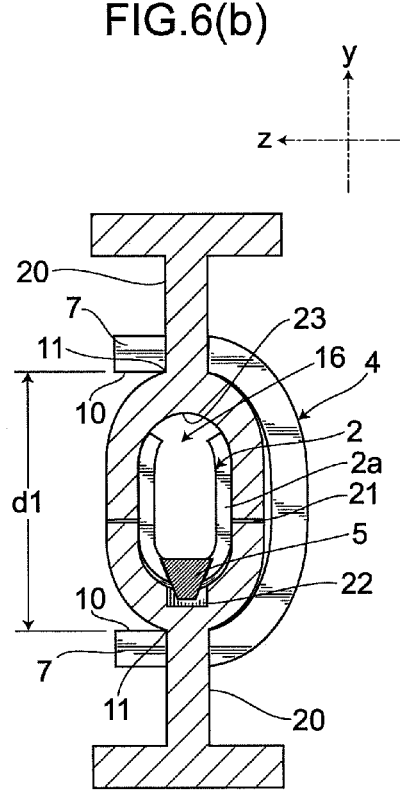

INTRAOCULAR LENS INSERTION DEVICES AND METHODS

CROSS-REFERENCE TO RELATED APPLICATIONS

This application is a continuation of U.S. application Ser. No. 12/997,651, now U.S. Pat. No. 8,382,769, which has a 35 U.S.C. §371(c) date of Jan. 17, 2011 and is the U.S. national stage of PCT application Ser. No. PCT/JP2009/060921, filed Jun. 16, 2009, each of which is incorporated herein by reference in its entirety.

TECHNICAL FIELD

The present invention relates to an intraocular lens insertion device suitable for use in an intraocular lens insertion device used to implant an intraocular lens into an aphakic eye after cataract surgery.

BACKGROUND ART

In cataract surgery, there has been widely performed a method in which an opacified lens is removed by means of phacoemulsification (PEA), followed by implanting the intraocular lens into an eye as a replacement for the crystalline lens thus removed. Such intraocular lens comprises an optical portion acting as a lens and a supporting portion that allows the intraocular lens to be held in the eye by positioning the intraocular lens on an eye axis. Further, the intraocular lenses broadly include a hard intraocular lens whose optical portion is made of a hard material such as polymethylmethacrylate or the like, and a soft intraocular lens whose optical portion is made of a soft material such as soft acrylic, silicone or the like.

The hard intraocular lens is inserted into the eye through an incision formed on the cornea or the sclera, which incision is as long as or longer than the diameter of the optical portion which is 6 mm. In contrast, the soft intraocular lens can be folded due to the flexibility thereof, thus making it possible to be inserted into the eye through an incision having a width of 4 mm or shorter, which width is shorter than the diameter of the optical portion. Further, insertion through a further smaller incision becomes possible when using a dedicated insertion device.

Narrowing the width of the incision reduces the burden imposed on a patient going through the surgery, and the possibility of corneal astigmatism caused by the surgery as well as incision infections. In this sense, the soft intraocular lens tends to be preferred.

An intraocular lens insertion device generally comprises an insertion device main body and an insertion tube. Such insertion tube has been used mainly in a disposable fashion in view of sanitation requirements. However, a type of insertion device that is disposable as a whole has been available, in which the insertion device main body and the insertion tube have a one-piece structure.

A type of disposable insertion tube that allows an operator or an assistant to place the intraocular lens thereinside at the time of operation is generally called a cartridge, and is made of synthetic resin such as polypropylene or the like. If the insertion tube is disposable, the insertion device main body is generally made of a metal and can be used for multiple times.

The operator injects into the cartridge an appropriate amount of a viscoelastic substance such as hyaluronic acid or the like, and then, places the intraocular lens in a lens placement section of the cartridge, followed by attaching to the insertion device main body the cartridge in which the intraocular lens has been placed. Then, the operator inserts through the aforementioned incision into an eye a nozzle section provided on an end of the cartridge, and releases the intraocular lens into an eyeball from a discharge port of the nozzle section by pushing the intraocular lens placed in the vicinity of a proximal end of the cartridge with an end of a plunger which is one of the components of the insertion device main body. In general, the lumen of the cartridge becomes narrower from the lens placement section provided on the proximal end of the cartridge toward an end of the nozzle section, thereby making it possible to fold the intraocular lens further smaller.

With regard to the cartridge, there has been disclosed, for example, an intraocular lens implantation device that allows the intraocular lens to be placed in the lumen of the cartridge in a folded fashion by first placing the intraocular lens in a placement section equipped with a hinge and then closing such hinge (e.g., see patent document 1). Further, there has also been disclosed an intraocular lens injector cartridge that allows an intraocular lens to be placed in an unfolded fashion through a lens insertion port of the cartridge (e.g., see patent document 2).

Furthermore, there has been disclosed an intraocular lens insertion device that allows the intraocular lens to be placed through the lens insertion port of the cartridge in a manner such that the intraocular lens is folded to some extent when being placed (e.g., see patent document 3).

In addition, from the perspective of a method of placing the intraocular lens, the structures of the cartridges disclosed in the patent document 2 and the patent document 3 are simpler than that of the cartridge disclosed in the patent document 1. Further, since the cartridges disclosed in the patent document 2 and the patent document 3 do not require folding by a hinge, the intraocular lens can be comparatively easily placed.

REFERENCE

Patent document 1: Japanese Unexamined Patent Application Publication No. Hei 8-505540
Patent document 2: Japanese Unexamined Patent Application Publication No. 2002-541912
Patent document 3: WO 2005/070341

DISCLOSURE OF THE INVENTION

Problem to be Solved by the Invention

However, a circumferential edge of the optical portion of the intraocular lens to be pushed by a plunger is extremely thin (often being 0.3 mm or less). Further, the end of the plunger is formed extremely small, since the intraocular lens is released from a small discharge port of the nozzle of the cartridge. In this sense, there are problems that it is extremely difficult to position the end of the plunger with respect to the circumferential edge of the optical portion of the intraocular lens.

For example, if there is provided a larger lens insertion port of the cartridge so as to make it easy to place the intraocular lens in the cartridge, the position of the intraocular lens inside the cartridge cannot be settled, thereby making it impossible, at times, to accurately position the end of the plunger with respect to the circumferential edge of the optical portion of the intraocular lens when directly attaching the cartridge to the insertion device main body. In this case, when trying to release the intraocular lens under the aforementioned condition, as a cartridge 100 shown in FIGS. 8(a) and 8(b), an intraocular lens 101 may climb on a plunger 102 (FIG. 8(a)), and the plunger 102 may climb on the intraocular lens 101 (FIG. 8(b)), thereby making it impossible for the plunger 102 to capture the circumferential edge of an optical portion 103 of the intraocular lens 101. In this sense, there are problems that the intraocular lens 101 cannot be appropriately released, and the intraocular lens 101 itself may be damaged.

Further, in order to accurately position the intraocular lens inside the cartridge, the lens insertion port of the cartridge may be formed small. However, if a clearance between the intraocular lens and an inner wall of the cartridge at a spot where the intraocular lens is to be placed is formed too small, it becomes difficult to place the intraocular lens in the cartridge, and the intraocular lens itself may be damaged or dropped at the time of placement, and thus one may fail to appropriately place the intraocular lens.

Therefore, in view of the aforementioned problems, it is an object of the present invention to provide an intraocular lens insertion device allowing an intraocular lens to be easily placed and capable of easily positioning the intraocular lens placed in a lens placement section.

Means for Solving the Problem

In order to achieve the aforementioned object, the invention according to a first aspect is an intraocular lens insertion device comprising an insertion tube having a lens placement section in which an intraocular lens is to be placed, and capable of releasing the intraocular lens from a nozzle section of the insertion tube to the outside by pushing the intraocular lens with a plunger. Such intraocular lens insertion device further has a deforming means for deforming the lens placement section when attaching the insertion tube to the insertion device main body, thereby positioning the intraocular lens in the lens placement section.

Further, the invention according to a second aspect is an intraocular lens insertion device comprising an insertion tube having a lens placement section in which an intraocular lens is to be placed and an insertion device main body to which the insertion tube is attached. Such intraocular lens insertion device is capable of releasing the intraocular lens from a nozzle section of the insertion tube to the outside by pushing the intraocular lens with a plunger. Such intraocular lens insertion device further has a deforming means for deforming the lens placement section when attaching the insertion tube to the insertion device main body, thereby positioning the intraocular lens in the lens placement section. Such deforming means includes an abutting surface provided on the insertion device main body and an abutted surface provided on the outer circumference of the insertion tube. The abutting surface is specifically provided on an attaching portion for fixing the insertion tube to the insertion device main body. When fixing the insertion tube to the attaching portion, the abutting surface is allowed to push against the abutted surface, thereby deforming the lens placement section.

Furthermore, according to the invention described in a third aspect, a slit is provided on the aforementioned lens placement section Furthermore, according to the invention described in a fourth aspect through a sixth aspect, the aforementioned insertion tube is a cartridge.

Effects of the Invention

The intraocular lens insertion device of the present invention allows the intraocular lens to be easily placed and is capable of easily positioning the intraocular lens placed in the lens placement section, thereby making it possible to reduce the possibility of the occurrence of scratches on or breakage of the intraocular lens when placing and releasing the intraocular lens.

BRIEF DESCRIPTION OF THE DRAWINGS

FIGS. 6(a) and 6(b) are sectional views showing the cartridge according to the embodiment of the present invention when viewed from the rear end thereof, with FIG. 6(a) showing a state in which the cartridge has not yet been attached to the insertion device main body and FIG. 6(b) showing state in which the cartridge has been attached to the insertion device main body.

BEST MODE FOR CARRYING OUT THE INVENTION

An embodiment of the present invention is described hereunder with reference to the accompanying drawings. In the beginning, the overall structure of the present embodiment is described.

(1) Overall Structure

Figure 1:
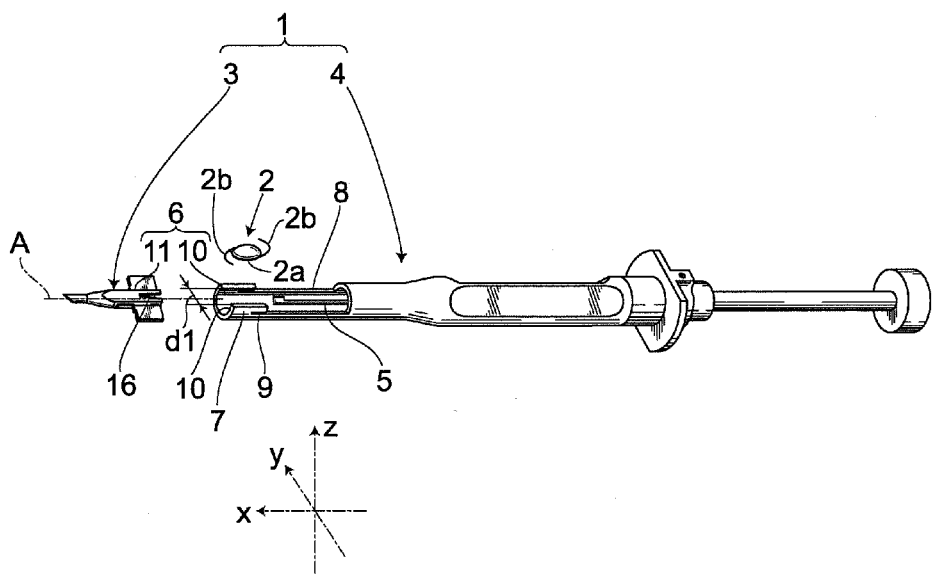
FIG. 1 is a schematic view showing an overall structure of an intraocular lens insertion device according an embodiment of the present invention.

An intraocular lens insertion device 1 shown in FIG. 1 comprises a cartridge 3 serving as an insertion tube in which an intraocular lens 2 is to be placed, and an insertion device main body 4 having a plunger 5 for pushing out the intraocular lens thus placed into an eye ball.

In addition to the aforementioned structure, the intraocular lens insertion device 1 further has a deforming means 6 for deforming the cartridge 3 so as to allow the plunger 5 to abut against the intraocular lens 2 at a predetermined position.

The insertion device main body 4 has an attaching portion 7 and a guiding portion 8 for guiding the cartridge 3 to the attaching portion 7 so that the cartridge 3 is attached to the attaching portion 7. The guiding portion 8, at an end thereof, is connected to the attaching portion 7. A pair of the attaching portions 7 is provided on an end of a forward direction x of a lens advancement axis A of the insertion device main body 4. Further, the pair of the attaching portions 7 is provided with attaching grooves 9 communicated respectively with the guiding portion 8 and a pair of abutting surfaces 10 facing each other. In addition, the distance between the abutting surfaces 10 is denoted by d1.

In this way, the intraocular lens insertion device 1 is capable of inserting the intraocular lens 2 folded small into an eye by pushing out the intraocular lens 2 placed in the cartridge 3 with the plunger 5.

Here, in the intraocular lens insertion device 1, the cartridge 3 is integrated into the insertion device main body 4 after being attached to the insertion device main body 4. And, at the same time, the deforming means 6 becomes capable of holding the posture of the intraocular lens 2 at a predetermined position. Such deforming means 6 includes an abutting surface 10 provided on an inner side of the attaching portion 7 and an abutted surface 11 formed on an outer periphery side surface of the cartridge 3.

Here, since the intraocular lens insertion device 1 of the present invention is a medical device, the materials of the members composing the intraocular lens insertion device 1 have to be physically and chemically stable. Specifically, for materials of members to be inserted into an eye, those that have been proven biologically safe must be employed. Such materials include, for example, those approved by FDA (Food and Drug Administration of U.S.A.) as implant materials, those standardized by ISO (International Organization for Standardization) as implant materials, and materials that have passed the tests according to ISO10993. For materials meeting such requirements, for example, polyethylene, polypropylene or the like can be employed as the material of the cartridge 3, and titanium alloys, martensitic stainless steels can be employed as the material of the plunger 5.

The intraocular lens 2 is made of a soft material that is foldable, such as silicon resin, acrylic resin, hydrogel or the like. The intraocular lens 2 is unfolded after being released into an eyeball, and serves as a replacement for the crystalline lens. Further, the intraocular lens 2 has an optical portion 2a and two supporting portions 2b, 2b.

The optical portion 2a functions as a lens capable of refracting light entering into an eyeball and allowing an image to be formed on the retina. Further, the optical portion 2a is formed into a flattened shape having a predetermined thickness.

The two supporting portions 2b, 2b are provided for supporting the optical portion 2a at a predetermined position in an eyeball. Further, the two supporting portions 2b, 2b extend from two symmetrical points on the circumference of the optical portion 2a, respectively, in a manner such that the two supporting portions 2b, 2b extended in an arc away from an outer circumference of the optical portion 2a, and have a curvature slightly larger than that of the outer circumference of the optical portion 2a.

Figure 2:
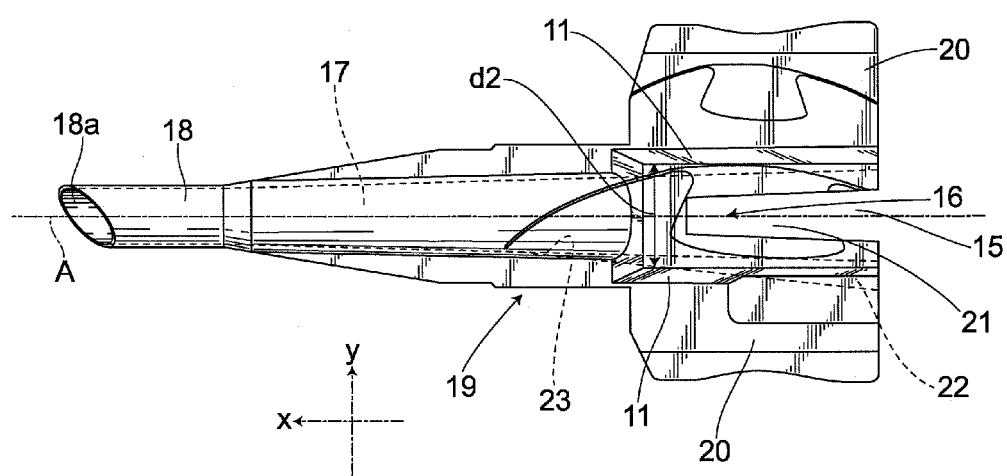
FIG. 2 is a plan view showing the structure of a cartridge according to the embodiment of the present invention.

Next, a structure of the cartridge 3 is described with reference to FIG. 2. The cartridge 3 comprises a cartridge main body 19 in which a lens insertion port 15, a lens placement section 16, a transition section 17 and a nozzle section 18 are successively provided along the lens advancement axis A, and wing portions 20, 20 extending from both side surfaces of the cartridge main body 19 along a sidewise direction y orthogonal to a lens advancement direction x.

The lens insertion port 15 is provided as an opening having a shape obtained by connecting a pair of semicircles with straight lines. The length of the lens insertion port 15 in the sidewise direction y orthogonal to the forward direction x of the lens advancement axis A, is formed longer than the length of the optical portion 2a (the radius of the optical portion 2a) of the intraocular lens 2 folded in half. Further, a slit 21 is provided on both an upper surface and an under surface of the lens insertion port 15, in the form of a cutout extending in the lens advancement direction x. Namely, the slit 21 comprises a pair of cutouts provided on surfaces of the lens insertion port 15 that are facing each other. Further, the slit 21 is formed into a trapezoidal shape gradually narrowing from the lens insertion port 15 toward the lens placement section 16.

Further, the lens placement section 16 is provided in front of the lens insertion port 15 with respect to the lens advancement axis A, and the transition section 17 is provided in front of the lens placement section 16 with respect to the lens advancement axis A. In addition, the length of the lens placement section 16 in the sidewise direction y is substantially the same as that of the lens insertion port 15. Namely, the length of the lens placement section 16 in the sidewise direction y is formed longer than the length of the optical portion 2a (the radius of the optical portion 2a) of the intraocular lens 2 folded in half.

An inner wall of the transition section 17 is formed into the shape of a mortar, gradually narrowing toward a distal end thereof, which distal end is communicated with the nozzle section 18. A groove 22 is provided on a lumen 23 formed between the lens placement section 16 and the transition section 17. Such groove 22 is so formed that it becomes possible for the plunger 5 to more reliably capture the intraocular lens 2 with a substantial center portion of a distal end surface thereof.

In this way, the cartridge main body 19 is so formed that the intraocular lens 2 placed in the lens placement section 16 through the lens insertion port 15 can successively move from the lens placement section 16 to the transition section 17, and then from the transition section 17 to the nozzle section 18, after being pushed by the plunger toward the forward direction of the lens advancement axis A. Further, the cartridge main body 19 is so formed that the intraocular lens 2 pushed by the plunger 5 can be released into an eye from a discharge port 18a of the nozzle section 18. In addition, the outer diameter of the nozzle section 18 is formed in to a shape that can be inserted into an incision (not shown).

In addition to the aforementioned structure, the cartridge 3 of the present invention is provided with the abutted surface 11 abutting against the abutting surface 10 provided on the attaching portion 7. According to the present embodiment, the abutted surface 11 is a flat surface, and is provided on both side surfaces of a rear portion of the cartridge 3 so that a distance d2 between the abutted surfaces 11 becomes larger than the distance d1 between the two abutting surfaces 10 of the attaching portion 7, and the abutted surface 11 can be abutted by the abutting surface 10. Here, the distance between the abutted surfaces 11 is denoted by d2. According to the present embodiment, the cartridge 3 and the attaching portion 7 are so formed that the distance d2 between the abutted surfaces 11 is larger than the distance d1 between the abutting surfaces 10.

(2) Operation and Effects

In the aforementioned structure, a visco-elastic substance such as ophthalmologic hyaluronic acid pharmaceuticals or the like is loaded into the lens placement section 16, using an infusion device. Subsequently, the intraocular lens 2 is folded in half, namely, into a substantial U shape in a manner such that a pair of the supporting portions 2b extends to the outside, using a storage container (not shown) having a mechanism capable of folding the intraocular lens 2 in half. Tweezers 25 are then used to pick and hold such intraocular lens 2 folded in half.

Figure 3:
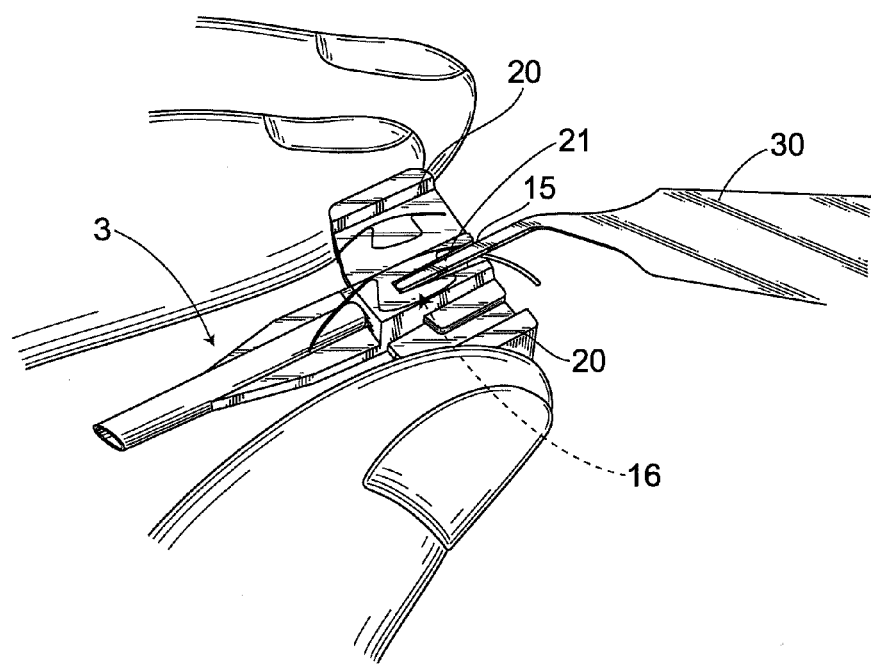
FIG. 3 is a diagram showing a method of inserting an intraocular lens into the cartridge according to the embodiment of the present invention.
Figure 4:
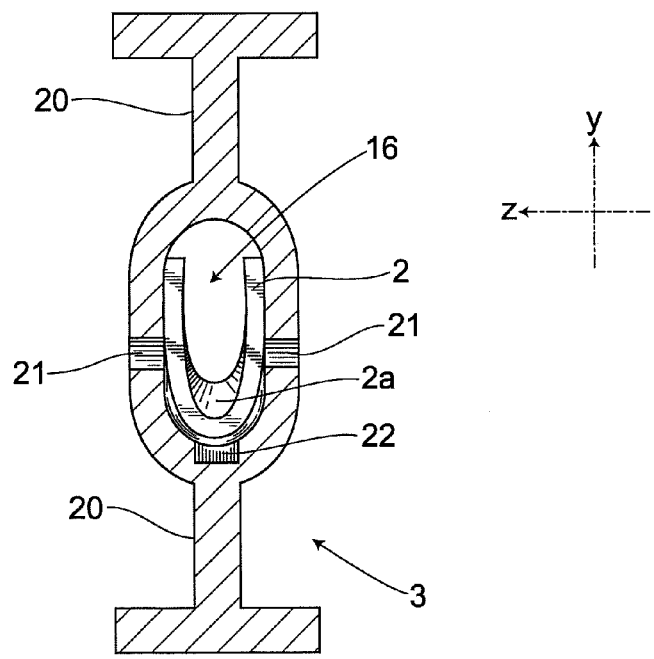
FIG. 4 is a sectional view showing the cartridge according to the embodiment of the present invention when viewed from a rear end thereof and when the intraocular lens is placed therein.

Subsequently, as shown in FIG. 3, the intraocular lens 2 is inserted into the lens insertion port 15 beginning with one of the supporting portions 2b thereof after adjusting the center portion of the optical portion 2a of the intraocular lens 2 held by tweezers 25 to a side on which the groove 22 is formed while holding with fingers the two wing portions 20 provided on both sides of the cartridge 3. Tweezers 25 are then removed from the slit 21 after being used to insert the intraocular lens 2 into the cartridge 3 through the lens insertion port 15 and place the intraocular lens 2 in the lens placement section 16. In this way, the intraocular lens 2 is so placed that the optical portion 2a thereof is positioned above the groove 22 of the lens placement section 16 (FIG. 4).

Here, the length of the lens insertion port 15 in the sidewise direction y orthogonal to the forward direction x of the lens advancement axis A, is formed longer than the length of the optical portion 2a (the radius of the optical portion 2a) of the intraocular lens 2 folded in half. Therefore, a clearance is formed between the intraocular lens 2 and the lumen 23 in the sidewise direction y. In this sense, it becomes easy for an operator to place the intraocular lens 2 in the lens placement section 16, thereby reducing the possibility of the occurrence of scratches on or breakage of the intraocular lens 2 when placing the intraocular lens 2 in the lens placement section 16.

Further, since the slit 21 is provided on the cartridge 3, it is easy to remove the tweezers 25 used to place the intraocular lens 2 in the lens placement section 16, thereby making it easier to place the intraocular lens 2 in the lens placement section 16.

The wing portion 20 of the cartridge 3 holding the intraocular lens 2 therewithin is then placed on the guiding portion 8 of the insertion device main body 4, followed by pushing such cartridge 3 toward a distal end of the guiding portion 8. As a result, the wing portion 20 is inserted into the attaching groove 9, and, at the same time, the abutted surface 11 is allowed to abut against the abutting surface 10. In this way, the cartridge 3 in which the intraocular lens 2 has been placed is attached to the insertion device main body 4.

Figure 5:
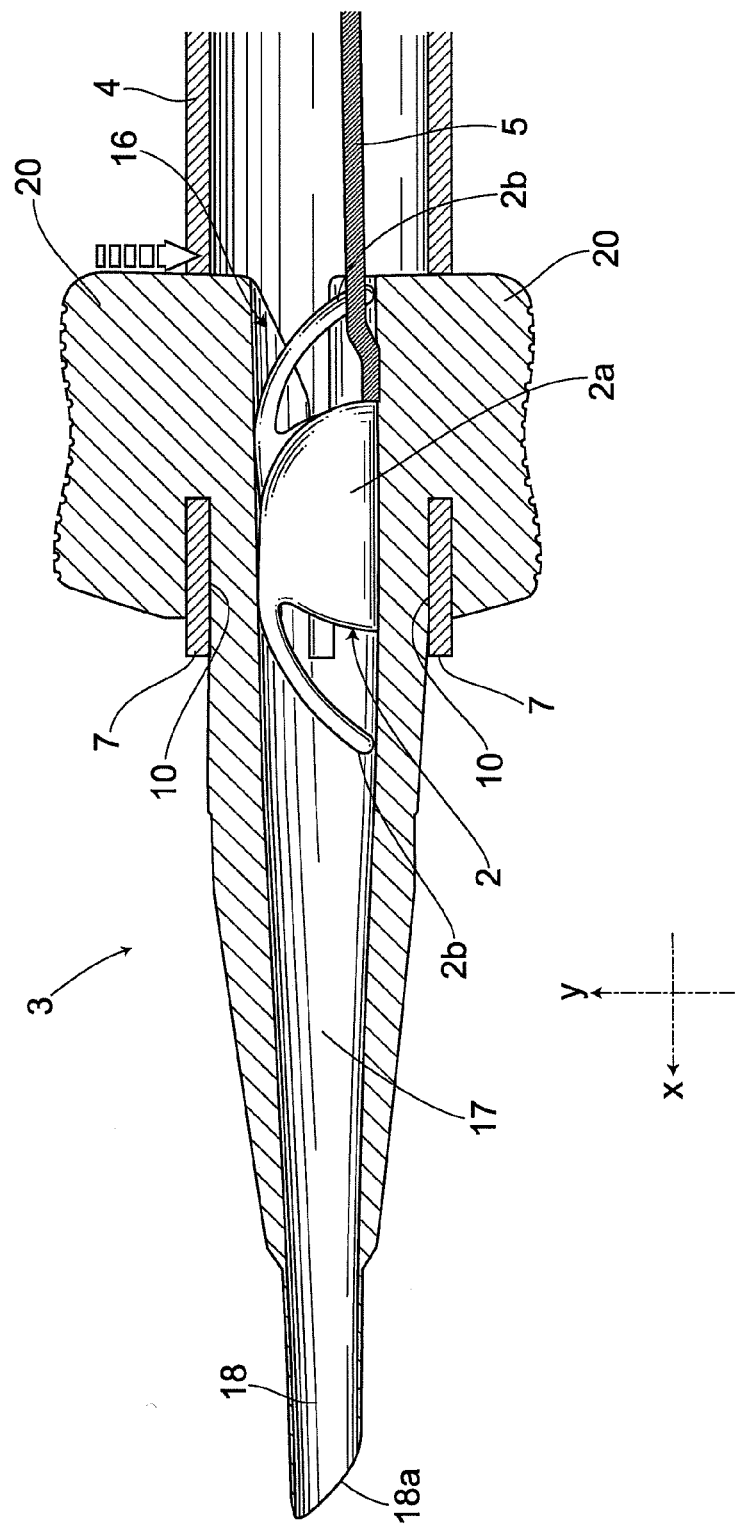
FIG. 5 is a top cross-sectional view of an insertion device main body according to the embodiment of the present invention, showing a state in which the cartridge is secured to the insertion device main body of the insertion device main body.

At that time, the abutted surface 11 of the cartridge 3 is allowed to be abutted by the abutting surface 10 of the attaching portion 7 due to the difference between the distance d1 and the distance d2 (FIGS. 6(a) and 6(b)). However, since the cartridge 3 is made of a flexible material, the slit 21 starts to be deformed inwardly when further pushing the cartridge 3 in the forward direction. As the cartridge 3 continues to be squeezed between the two attaching portions 7, the open space of the slit 21 gradually becomes narrow, causing the lens placement section 16 to undergo deformation in a diameter-decreasing direction thereof. Namely, the lumen 23 gradually narrows as the lens placement section 16 is being so deformed that its length in the sidewise direction y becomes shorter. In this way, the intraocular lens 2 placed in the lens placement section 16 is allowed to come into close contact with the lumen 23 of the lens placement section 16 (FIG. 5).

According to the intraocular lens insertion device 1 of the present embodiment, the abutted surface 11 is provided on the cartridge 3, and the abutting surface 10 provided on the attaching portion 7 of the insertion device main body 4 is allowed to press against such abutted surface 11. Thus, due to the flexibility of the material of the cartridge 3 itself, the lens placement section 16 can be gradually narrowed in the sidewise direction y by only inserting the cartridge 3 into the attaching portion 7 of the insertion device main body 4 so as to attach the cartridge 3 to the insertion device main body 4.

In this way, the intraocular lens 2 is allowed to come into close contact with the lumen 23 of the lens placement section 16, and an upper portion of the substantial U shape of the folded intraocular lens 2 is allowed to abut against the lumen 23 of the lens placement section 16. Namely, the clearance between the intraocular lens 2 and the lumen 23 in the lens placement section 16, in the sidewise direction y, is eliminated for the first time after attaching the cartridge 3 to the insertion device main body 4, thereby making it possible to hold the posture of the intraocular lens 2 at the predetermined position (FIG. 6(b)).

Further, according to the intraocular lens insertion device 1 of the present embodiment, the cartridge 3 is provided with the slit 21, thereby making it possible for the lens placement section 16 to be easily deformed inwardly in the sidewise direction y. Therefore, the intraocular lens insertion device 1 is capable of further reliably holding the posture of the intraocular lens 2 at the predetermined position.

As described above, the intraocular lens insertion device 1 of the present invention is capable of further reliably positioning the intraocular lens 2 in the lens placement section 16 by only attaching the cartridge 3 to the attaching portion 7. Therefore, no special manipulation is required for the operator or an assistant to position the intraocular lens 2. Further, no practice is required to be able to further reliably position the intraocular lens 2.

Subsequently, when the operator pushes the plunger 5, a distal end portion of the plunger 5 is allowed to abut against the circumference of the optical portion 2a of the folded intraocular lens 2 placed in the lens placement section 16. Here, since the intraocular lens 2 is positioned in the lens placement section 16, it is possible to further reliably capture the circumference of the optical portion 2a with the distal end portion of the plunger 5 (FIG. 5).

As described above, the intraocular lens insertion device 1 of the present invention is capable of further reliably holding the posture of the intraocular lens 2 at the predetermined position, thereby making it possible for the distal end portion of the plunger 5 to further reliably capture the circumference of the optical portion 2a of the folded intraocular lens 2 in the cartridge 3 when the operator pushes the plunger 5. Therefore, the intraocular lens insertion device 1 is capable of reducing the possibility of the occurrence of scratches on or breakage of the intraocular lens 2 when pushing out the intraocular lens 2.

In this way, according to the intraocular lens insertion device 1, as the plunger 5 continues to push the intraocular lens 2 from the lens placement section 16, the upper portion of the substantial U shape of the folded intraocular lens 2 is gradually folded inwardly, thereby causing the intraocular lens 2 itself to be folded into a substantial circular shape and further smaller as compared to the moment when the intraocular lens 2 is inserted into the lens placement section 16 through the lens insertion port 15, thus making it possible to implant the intraocular lens 2 into the eye ball through a further smaller incision.

An embodiment of the present invention has thus been described. However, the present invention is not limited to the aforementioned embodiment, and various modified embodiments of the present invention are possible.

Figure 7A:
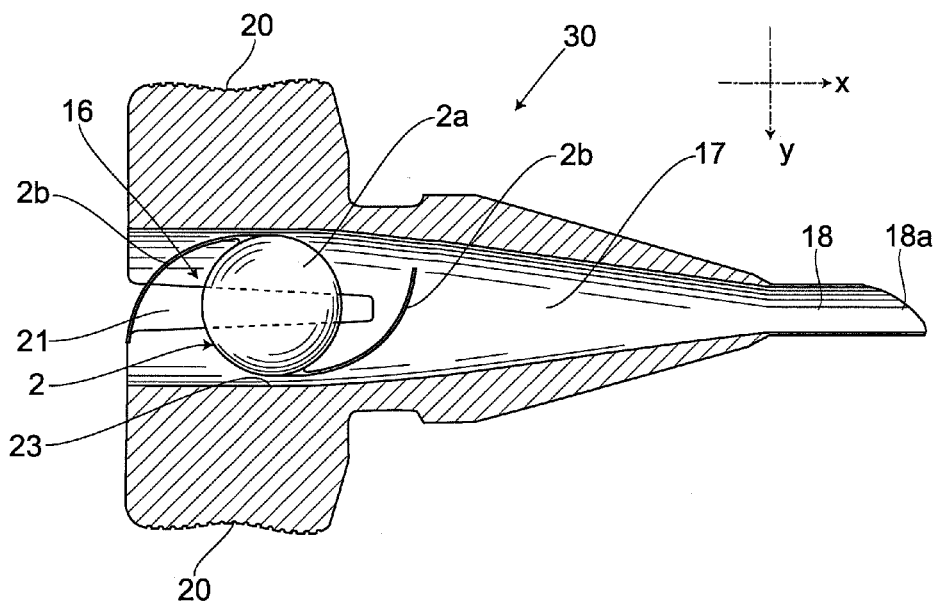
FIGS. 7(a) and 7(b) are top cross-sectional views showing a rear end of a cartridge according to a variation of the present invention, with FIG. 7(a) showing a state in which the cartridge has not yet been attached to the insertion device main body and FIG. 7(b) showing state in which the cartridge has been attached to the insertion device main body.

For example, the aforementioned embodiment described a case in which the intraocular lens 2 is folded into a U shape. However, the present invention is not limited to such case, and can be applied to a cartridge 35 that allows an unfolded intraocular lens 2 to be placed flatwise in the lens placement section 16. In this case, the length of the lens insertion port 15 in the sidewise direction y is formed longer than the diameter of the optical portion 2a of the intraocular lens 2, thereby making it easy to place the intraocular lens 2 in the lens placement section 16 (FIG. 7(a)).

Figure 7B:
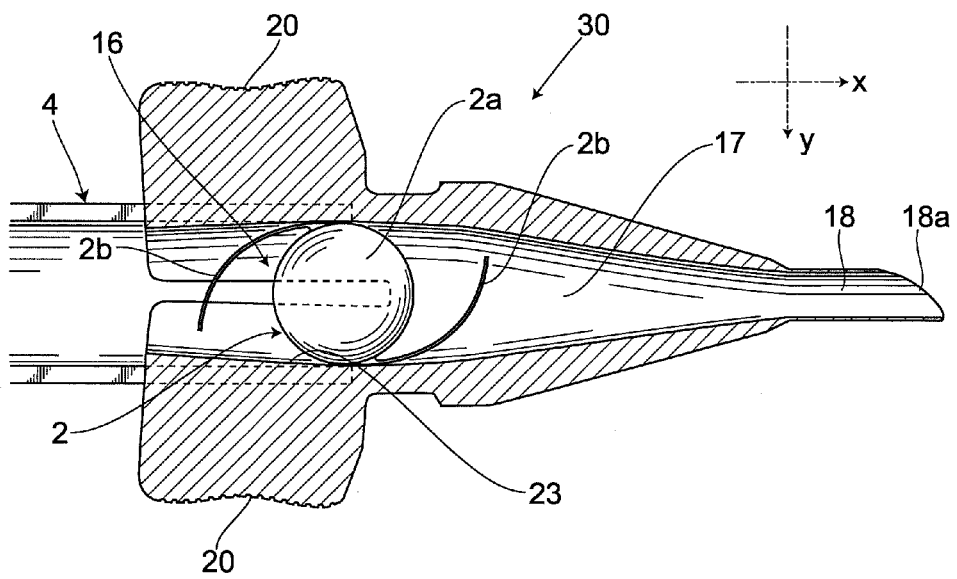
Figure 8A:
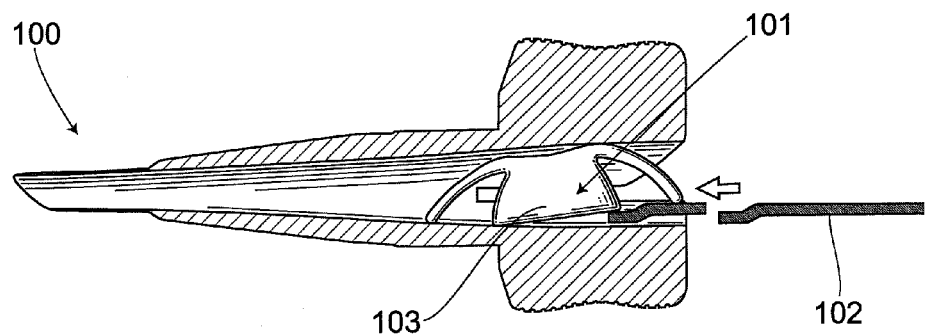
FIGS. 8(a) and 8(b) are top cross-sectional views showing a cartridge of a conventional intraocular lens insertion device, with FIG. 8(a) showing a use condition 1 and FIG. 8(b) showing a use condition 2.
Figure 8B:
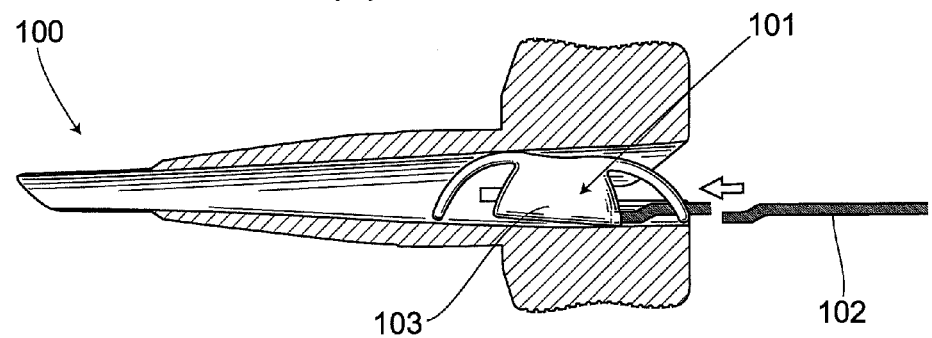

Further, the cartridge 35 of the present variation is provided with the slit 21 and the abutted surface 11, and the abutting surface 10 provided on the attaching portion 7 of the insertion device main body 4 is allowed to press against the abutted surface 11. Therefore, the cartridge 3 is so deformed that the length of the lens placement section 16 in the sidewise direction y becomes shorter after attaching the cartridge 3 in which the intraocular lens 2 is placed to the insertion device main body 4 (FIG. 7(b)). In this way, according to a cartridge 30, the lumen 23 of the lens placement section 16 is allowed to come into close contact with the circumference of the optical portion 2a of the intraocular lens 2, thereby making it possible to further reliably position the intraocular lens 2.

Furthermore, the intraocular lens 2 does not necessarily have to be folded into a substantial U shape. The intraocular lens 2 can be folded into various cross-sectional shapes such as a J shape or an O shape.

Furthermore, explanation was made on a case in which the slit 21 is provided as a supplementary means for easily deforming the lens placement section 16. However, other supplementary means can be employed as well, including thinning a certain portion of the cartridge 3, using a soft material to form a certain portion of the cartridge 3 and the like.

Furthermore, according to the aforementioned embodiment, the deforming means 6 including the abutting surface 10 and the abutted surface 11 is provided. However, the present invention is not limited to such configuration. As a variation, the deforming means 6 may include at least one protrusion not in the form of a surface but in the form of a dot as long as the distance d2 is larger than the distance d1 so that the length of the lens placement section 16 in the sidewise direction y becomes shorter via deformation. In addition, in this case, at least one protrusion may be provided on both the abutting surface 10 and the abutted surface 11, and may also be provided only on either the abutting surface 10 or the abutted surface 11 as long as the distance d2 is larger than the distance d1.

However, since there are few advantages with the difference between the distance d2 and the distance d1 being less than 0.1 mm as far as the ease of inserting the intraocular lens 2 is concerned, the difference between the distance d2 and the distance d1 is preferably 0.1 mm or larger.

The invention claimed is:

1. A method of positioning an intraocular lens that has been placed within a lens placement section of a removable cartridge, the lens placement section including an inner surface, the method comprising the steps of:
compressing the lens placement section of the removable cartridge with a portion of an insertion device main body such that portions of the lens placement section inner surface are moved closer to one another by the insertion device main body as the removable cartridge is being attached to the insertion device main body; and
maintaining the compression of the lens placement section after the removable cartridge has been attached to the insertion device main body.

2. A method as claimed in claim 1, wherein
the removable cartridge defines a lens advancement axis; and
the step of compressing the lens placement section comprises compressing the lens placement section in a direction that is transverse to the lens advancement axis.

3. A method as claimed in claim 1, wherein
the insertion device main body defines a longitudinal axis and includes a cartridge attaching portion with first and second abutting surfaces on opposite sides of the longitudinal axis; and the step of compressing the lens placement section comprises compressing the lens placement section with the first and second abutting portions.

4. A method as claimed in claim 3, wherein
the removable cartridge defines first and second exterior surfaces that are aligned with the lens placement section; and
the step of compressing the lens placement section comprises applying compression force to the first and second exterior surfaces of the removable cartridge with the first and second abutting portions of the insertion device main body.

5. A method of positioning an intraocular lens that has been placed within a lens placement section of a removable cartridge, the removable cartridge including a main body in which the lens placement section is located and the main body includes first and second slots that are coextensive with at least a portion of the lens placement section, the method comprising the steps of:
compressing the lens placement section of the removable cartridge, at first and second locations that are longitudinally aligned with, and circumferentially offset from, the first and second slots, with a portion of an insertion device main body as the removable cartridge is being attached to the insertion device main body; and
maintaining the compression of the lens placement section after the removable cartridge has been attached to the insertion device main body.

6. A method of positioning an intraocular lens that has been placed within a lens placement section of a removable cartridge that includes first and second wing portions, the method comprising the steps of:
compressing the lens placement section of the removable cartridge by inserting the first and second wing portions into first and second grooves of an insertion device main body that are configured to receive the first and second wing portions as the removable cartridge is being attached to the insertion device main body; and
maintaining the compression of the lens placement section after the removable cartridge has been attached to the insertion device main body.

7. A method of operating an intraocular lens insertion device, comprising the steps of:
placing an intraocular lens into a lens placement section of a removable cartridge, the lens placement section including an inner surface; and
after the placing step, attaching the removable cartridge to an insertion device main body that is configured to compress the lens placement section such that portions of the lens placement section inner surface are moved closer to one another by the insertion device main body as the removable cartridge is being attached to the insertion device main body and is also configured to maintain the compression of the lens placement section after the cartridge has been attached to the insertion device main body.

8. A method as claimed in claim 7, further comprising the step of:
pushing the intraocular lens out of the compressed removable cartridge with a plunger.

9. A method as claimed in claim 7, wherein
the insertion device main body includes a plunger; and
the compression of the lens placement section during the attaching step aligns the intraocular lens with the plunger.

10. A method as claimed in claim 7, wherein
the removable cartridge defines a lens advancement axis; and the lens placement section is compressed in a direction that is transverse to the lens advancement axis during the attaching step.

11. A method as claimed in claim 7, wherein
the insertion device main body defines a longitudinal axis and includes a cartridge attaching portion with first and second abutting surfaces on opposite sides of the longitudinal axis; and the lens placement section is compressed by the first and second abutting portions during the attaching step.

12. A method as claimed in claim 11, wherein
the removable cartridge defines first and second exterior surfaces that are aligned with lens placement section; and the first and second abutting portions of the insertion device main body apply compression force to the first and second exterior surfaces of the removable cartridge during the attaching step.

13. A method as claimed in claim 7, wherein
the removable cartridge includes a main body in which the lens placement section is located and the main body includes first and second slots that are coextensive with at least a portion of the lens placement section; and the lens placement section is compressed at first and second locations that are longitudinally aligned with, and circumferentially offset from, the first and second slots during the attaching step.

14. A method as claimed in claim 7, wherein
the removable cartridge includes first and second wing portions;

the insertion device main body includes first and second grooves configured to receive the first and second wing portions; and the lens placement section is compressed as the first and second wing portions into are inserted into first and second grooves during the attaching step.

\* \* \* \* \*